US010060931B2

(12) United States Patent
Donovan et al.

(10) Patent No.: US 10,060,931 B2
(45) Date of Patent: Aug. 28, 2018

(54) USE OF COMPLEX FORMS OF CALMODULIN-LIKE SKIN PROTEIN CLSP

(71) Applicant: L'OREAL, Paris (FR)

(72) Inventors: Mark Donovan, Berville (FR); Dominique Bernard, Vanves (FR)

(73) Assignee: L'OREAL, Paris (FR)

( * ) Notice: Subject to any disclaimer, the term of this patent is extended or adjusted under 35 U.S.C. 154(b) by 379 days.

(21) Appl. No.: 14/327,799

(22) Filed: Jul. 10, 2014

(65) Prior Publication Data

US 2014/0348816 A1     Nov. 27, 2014

Related U.S. Application Data

(62) Division of application No. 12/686,672, filed on Jan. 13, 2010.

(60) Provisional application No. 61/202,077, filed on Jan. 27, 2009.

(30) Foreign Application Priority Data

Jan. 13, 2009  (FR) .................................... 09 50162

(51) Int. Cl.
   *G01N 33/68*     (2006.01)
   *A61K 8/64*      (2006.01)
   *A61Q 19/08*     (2006.01)

(52) U.S. Cl.
   CPC ............ *G01N 33/6881* (2013.01); *A61K 8/64* (2013.01); *A61Q 19/08* (2013.01); *G01N 2333/4727* (2013.01); *G01N 2800/20* (2013.01)

(58) Field of Classification Search
   None
   See application file for complete search history.

(56) References Cited

U.S. PATENT DOCUMENTS

| | | | | |
|---|---|---|---|---|
| 7,098,004 | B2 * | 8/2006 | Mehul ..................... | A61K 8/64 435/69.1 |
| 2003/0104362 | A1 * | 6/2003 | Cottarel ................. | C07K 14/40 435/6.18 |
| 2004/0142335 | A1 | 7/2004 | Petersohn et al. | |
| 2004/0142357 | A1 * | 7/2004 | Lu ........................... | C07K 14/47 435/6.18 |
| 2010/0216165 | A1 | 8/2010 | Donovan et al. | |

FOREIGN PATENT DOCUMENTS

| | | |
|---|---|---|
| FR | 7 796 646 | 1/2001 |
| FR | 2 924 947 A1 | 6/2009 |
| WO | 01/07/604 | 2/2001 |

OTHER PUBLICATIONS

Johann Urschitz, et al., "A serial analysis of gene expression in sun-damaged human skin", Journal of Investigative Dermatology, Nature Publishing Group, GB, vol. 119, No. 1, Jul. 1, 2002, pp. 3-13.

Weinkle S. Baumann, "Improving elasticity: The science of aging skin", Cosmetic Dermatology 200703 US, vol. 20, No. 3, (Mar. 2007), pp. 168-172.

Bruno Mehul, et al., Influence of calcium on the proteolytic degradation of the calmodulin-like skin protein (calmodulin-like protein 5) in psoriatic epidermis., Experimental Dermatology, Jun. 2006, vol. 15, No. 6, pp. 469-477.

* cited by examiner

*Primary Examiner* — Suzanne M Noakes
*Assistant Examiner* — Jae W Lee
(74) *Attorney, Agent, or Firm* — Oblon, McClelland, Maier & Neustadt, L.L.P.

(57) ABSTRACT

The invention also relates to the use of these complex forms for the purposes of screening for biological or chemical compounds capable of modulating a biological activity of said complex forms and/or for preparing and/or improving a pluristratified cell model.

2 Claims, 1 Drawing Sheet

Specification includes a Sequence Listing.

USE OF COMPLEX FORMS OF CALMODULIN-LIKE SKIN PROTEIN CLSP

CROSS-REFERENCE TO RELATED APPLICATIONS

This application is a divisional of U.S. application Ser. No. 12/686,672 filed Jan. 13, 2010, and claims the benefit of U.S. application Ser. No. 61/202,077 filed Jan. 27, 2009 and FR 0950162 filed Jan. 13, 2009.

FIELD OF THE INVENTION

The present invention relates to the use of complex forms of calmodulin-like skin protein (CLSP), of peptide fragments of this protein or of analogues thereof, as a marker for evaluating a state of chronological ageing of an epithelium, and in particular of the epidermis.

DESCRIPTION OF THE BACKGROUND

Epithelia are tissues of which the cells are joined to and interlinked with one another and lie on a basal membrane. They form either an external covering, for example at the surface of the skin, or the epidermis, or an internal covering, at the surface of a mucosa. They can also form glands.

More specifically, these epithelia are structures of which the homeostasis results from the implementation of a finely regulated set of intracellular and extracellular signals acting at all the stages of cell proliferation, migration and differentiation, and also of the synthesis of the various extracellular matrix components. These signals can in particular result from the action of factors produced by keratinocytes.

The maintaining of the correct physiological functions of an epithelium involves, in particular, epithelial terminal differentiation and/or proteoglycan synthesis.

As regards more particularly the epidermis, it is an epithelium, conventionally divided up into a basal layer of keratinocytes containing, in particular, skin stem cells and constituting the germinative layer of the epidermis, a "spiny" layer constituted of several layers of polyhedral cells placed on the basal layer, a "granular" layer comprising one to three layers said to be of flattened cells containing distinct cytoplasmic inclusions, keratohyalin granules, and finally, a set of upper cells, called horny layer (or stratum corneum) constituted of keratinocytes at the terminal stage of their differentiation, called corneocytes.

The stratum corneum, the outermost part of the skin which performs the function of a barrier between the organism and the environment, and the hair shaft, the emerging part of the hair follicle which constitutes the head of hair, both represent the result of the keratinocyte differentiation process. Epidermal differentiation follows a process of maturation in which keratinocytes from the basal layer differentiate and migrate so as to result in the formation of corneocytes, which are completely keratinised dead cells. This differentiation is the result of perfectly coordinated phenomena which will result in the thickness of the epidermis being kept constant and thus ensure the homeostasis of the epidermis.

Many skin disorders or pathological conditions can result from a dysfunction of epidermal homeostasis.

Thus, in the case of aged skin, this dysfunction is generally manifested through the appearance of wrinkles (micro-relief and deep wrinkles), a loss of elasticity, a rough feel and dryness. From the histological point of view, a flattening of the dermo-epidermal junction and a decrease in thickness of the dermis and of the epidermis are observed. The collagen and glycosaminoglycan content decreases. The barrier function of the skin is impaired. All these phenomena are increased by chronic exposure to the sun.

Similarly, this dysfunction may be worsened in women during the menopause.

SUMMARY OF THE INVENTION

The present invention results more particularly from the characterization by the inventors in the stratum corneum, of complex forms of the CLSP protein, the expression of which is found to be modulated differently over the course of the chronobiological ageing of an epithelium.

DETAILED DESCRIPTION OF THE INVENTION

Figure 1:
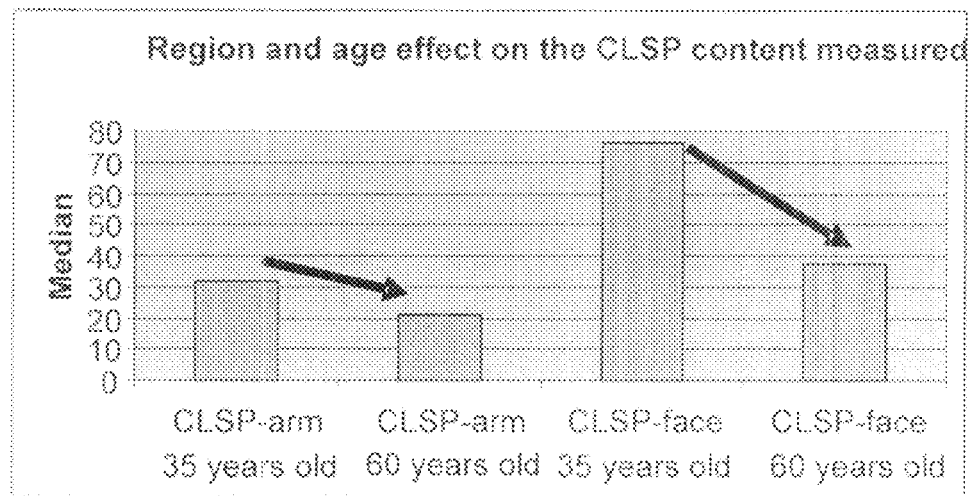
FIG. 1: it illustrates the relationship between age and the amount of complex forms according to the invention present in the skin of the forearm and of the face.

CLSP is a calcium-binding protein belonging to the calmodulin family, the precursor form of which comprises 146 amino acids. It has a molecular weight of approximately 16 kDa and an amino acid sequence homology of approximately 52% with calmodulin.

The structure of CLSP comprises 4 potential "EF-hand" calcium-binding sites, potential N-glycosylation sites, multiple potential phosphorylation sites and a myristylation site.

The binding of calcium to CLSP induces a change in its conformation which leads to its activation, enabling in particular its interaction with various target proteins.

An increase in the mRNA encoding CLSP has been shown over the course of photo-induced ageing (Urschitz, J. et al., J. Invest. Dermatol., 2002, 119:3-13) i.e. ageing resulting from repeated exposure of the skin to rays from the sun, a process distinct from that of chronological ageing, i.e. of physiological ageing linked to the passing of time.

For its part, document US 2004/0142335 observes, by means of a transcriptome analysis, an increase in the expression of the mRNA encoding the CLSP protein in skin of an aged individual compared with that of a young individual.

Thus, CLSP could in particular be involved in keratinocyte terminal differentiation (B. Mehul et al., J. Biol. Chem., 2000, Apr. 28; 275(17):12841-7), (EP 1 204 744).

More recently, the inventors have, unexpectedly, noted a decrease in the expression of particular forms of CLSP in the stratum corneum of aged human epidermis. Quite clearly, the forms characterized by the inventors correspond to stages of maturation of the protein which are distinct from those of the forms of CLSP considered up until now and in particular mentioned above.

As emerges from what follows, the complex forms have been characterized by the inventors by means of the implementation of a specific ELISA assay technique, in particular described in Example 1 hereinafter.

Thus, according to one of its aspects, the present invention relates to the use of at least one complex form of calmodulin-like skin protein, or CLSP, which derives at least in part from a polypeptide having an amino acid sequence encoded by a nucleic acid sequence represented completely or partly by SEQ ID NO 1, or an analogue thereof, or a fragment thereof, as a tool for the characterization, in particular in vitro or ex vivo, of a state of chronological ageing of an epithelium, and in particular of an epidermis.

Accordingly, the present invention relates to a method for the in vitro or ex vivo characterization of a state of chronological ageing of an epithelium comprising a step of determining at least one complex form of CLSP according to the invention, within said epithelium.

By "chronological ageing", within the meaning of the invention, it is intended to set aside from the scope of the invention the cutaneous phenomena which are consecutive to sun or U.V. exposure, namely the photo-induced skin ageing.

For the purpose of the present invention, the term "complex form" is intended to cover any conjugate of the CLSP protein or derivative thereof, with either another protein distinct from CLSP or a fragment thereof, or another CLSP protein or a fragment thereof.

For the purpose of the present invention, the term "derivative of the CLSP protein" denotes a fragment thereof or an analogue as defined hereinafter.

More specifically, a complex form may derive from the association of the whole CLSP protein or a fragment thereof, with either itself, or one of its fragments, or else with a target protein, or even with a protein structure such as a cornified envelope that has been proteolysed in the stratum corneum.

Thus, according to a first variant, the complex forms under consideration according to the invention may be dimer forms of the CLSP protein, or else the conjugate of two identical or different peptide fragments of this protein.

According to another variant, these complex forms may be the product resulting from the association of the CLSP protein or a fragment thereof, with a secondary target protein. By way of illustration of these target proteins capable of interacting with CLSP and/or a fragment thereof, mention may be made in particular of the 14.3.3 beta polypeptide, 14.3.3 sigma, annexins II and V, the calreticulins, ERp72, nucleolin, transglutaminase 3, MAGED1 (melanoma antigen gene D1), PPP4C (protein phosphatase 4) and USF2 (upstream transcription factor 2). They may also be peptide motifs such as the YWHAQ motif (14.3.3 tau).

Against all expectations, the inventors have noted that the quantification of these complex forms in the stratum corneum constitutes an effective and reliable means for defining the state of the corresponding epidermis. As specified above, a decrease in the expression of these complex forms is observed over the course of chronological ageing.

In this respect, a decrease in complex form(s) in accordance with the invention is indicative of a state of chronological ageing of an epithelium.

The characterization of these complex forms is therefore found to be of particular use for establishing a diagnosis of the state of an epidermis.

With regard to this diagnosis, it will be advantageously possible to offer the individual a cosmetic treatment that is most particularly suited to the profile of said individual. For obvious reasons, this type of personalization in terms of cosmetic treatment is particularly desired and liked by users. The present invention makes it possible to advantageously meet this demand.

According to another of its aspects, the present invention relates to a noninvasive, in particular cosmetic, method for characterizing, in particular in vitro or ex vivo, the chronological state of an epidermis, comprising at least the qualitative or quantitative characterization, in the stratum corneum of said epidermis, of the expression of at least one complex form of CLSP according to the invention.

According to one variant embodiment, the piece of data or value obtained via such a method may be assessed in comparison to a reference piece of data or value, obtained, for example, from at least one epithelium, in particular an epidermis, distinct from that which is the subject of the characterization, and the state of which is known.

According to one of its aspects, the present invention relates to a method for characterizing the chronological state of an epidermis as defined above, in which a decrease in complex forms in accordance with the invention is indicative of a state of chronological ageing.

According to another of its aspects, the present invention is also directed towards a noninvasive, in particular cosmetic, method for characterizing, in particular in vitro or ex vivo, the effectiveness of a cosmetic or therapeutic treatment intended to prevent and/or treat the signs of skin ageing linked to chronological ageing in an individual, such as wrinkles and fine lines, comprising at least the qualitative or quantitative characterization of at least one complex form of CLSP according to the invention.

The expression "signs of skin ageing" is intended to mean all the modifications of the external appearance of the skin due to chronological ageing, for instance wrinkles and fine lines, wizened skin, lack of elasticity and/or of tonicity of the skin, thinning of the dermis and/or degradation of the collagen fibres thereby leading to the appearance of slack and wrinkled skin.

The signs of skin ageing considered in the invention are those associated with or resulting from chronological skin ageing.

In particular, the signs of skin ageing considered in the invention are distinct from those associated with or resulting from the photo-induced skin ageing.

By "photo-induced ageing", it is intended to mean, in particular, the oxidative damages resulting from U.V exposure of the epidermis, and more particularly from U.V.A. exposure, resulting in the generation of free radicals, the glycation of proteins or the excessive activation of some cell surface receptors, and on tissue level, the thickening of elastin fibers.

Thus, the present invention is directed to the prevention and/or the treatment of the cutaneous manifestations associated with chronological skin ageing, and more particularly not associated with U.V. exposure.

The instant invention is more particularly directed to chronological skin ageing manifestations resulting from cell attrition and cell senescence.

Also, chronological ageing, on epidermis cells level, manifests itself by telomeres reduction, a decrease of cells stimulation due to hormones deficiencies, such as DHEA, or growth factors deficiencies, or due to a decrease in cell receptors numbers, and, on tissue level, notably by elastin fibers disappearance.

Such phenomena are not associated with an U.V. exposure, and, in consequence, are not associated with photo-induced skin ageing.

Cellular and tissue deficiencies subsequent to chronological skin ageing may result in xerosis, epidermis laxity, wrinkles and/or fine lines, cutaneous slackness, seborrheic keratose or cherry angioma.

More specifically, the method as described above may comprise at least the steps consisting in:

i. providing at least a first cutaneous surface sample representative of said individual, ii. quantifying, in said sample, especially via an ELISA assay technique, and in particular that described in Example 1 hereinafter, at least one complex form according to the invention, iii. repeating steps i. and ii. on a second skin surface sample representative of said individual, and iv. comparing the results obtained at the end of steps ii. and iii., in particular in order to deduce therefrom information relating to at least one effect of the treatment, said first and second skin surface samples corresponding to different treatment stages.

The reference value or piece of data in step ii. may be a piece of data obtained from the epithelium, in particular from the epidermis, representative of the individual who is the subject of the treatment, prior to the administration of said treatment or within a shorter chronological time in relation to the treatment start date.

According to one preferred embodiment, the first sample is representative of a pretreatment state and the second is representative of a state during the course of treatment or a post-treatment state.

According to one variant embodiment, the present invention relates to one of the methods above, in which an increase in complex form(s) is indicative of said treatment of the signs of skin ageing being effective.

According to one variant embodiment, one of the methods above may also comprise, at the end of the step of characterizing the complex forms of CLSP, at least one additional step aimed at administering, to said individual, a care composition, in particular a cosmetic care composition, established or selected with regard to the information obtained on said complex forms. This additional step may be consecutive to the characterization step.

According to one embodiment, this composition may also be selected from a range of compositions, each one of the latter being more particularly suitable for a type of information that may be obtained according to the method of the invention.

Thus, the advantage of the present invention is to propose a simple and rapid method, firstly for establishing the characterization of the physiological state of an epithelium, in particular of the epidermis of the skin and, secondly, for adjusting accordingly a treatment suitable for said epithelium or epidermis of the skin.

The methods of the invention may be carried out in vitro, ex vivo or in vivo.

As emerges from the description which follows, the methods according to the invention are particularly advantageous insofar as the implementation thereof does not require an invasive procedure.

This is because the localization, by the inventors, of these new biomarkers for ageing in the stratum corneum makes it possible to quantitatively or qualitatively characterize the expression of said markers by simple topical sampling.

Advantageously, this method may be carried out on a sample of stratum corneum of the individual under consideration, simply taken by stripping. The sampling method may, for example, be a stripping technique consisting in applying a portion of adhesive tape to the epithelium under consideration, such as an epidermis. On detaching this adhesive tape, a fraction of the epithelium, for example an epidermal fraction, is sampled. After protein extraction, said fraction is then analysed by means of an ELISA assay as considered in the present invention.

According to yet another aspect, the present invention also relates to the use of at least one complex form in accordance with the invention, as a tool for screening for biological or chemical compounds capable of modulating, and in particular of promoting, the increase in and/or the stability and/or the biological activity of these complex forms.

Accordingly, the present invention relates to a method for screening for biological or chemical compound capable of modulating the increase in and/or the stability and/or the biological activity of at least one complex form of CLSP according to the invention, comprising a step of contacting at least said complex form with at least one biological or chemical compound to be screened.

In particular, it relates to a method of screening for anti-ageing active agents, comprising at least the steps consisting in:

a) bringing at least one cell type containing at least one complex form in accordance with the invention into contact with at least one test chemical or biological compound, under conditions suitable for a manifestation of the expression of said form, and b) determining a content of at least one of said complex forms, c) comparing said content determined in step b) with a content of said complex form determined in the absence of test chemical or biological compound.

According to one variant embodiment, the present invention relates to a method as defined above, in which an increase in complex form(s) in accordance with the invention is indicative of an active agent with anti-ageing properties.

Thus, advantageously, a step of selecting the active agent(s) for which an increase in the content of complex form(s) in accordance with the invention is observed may further be carried out, at the end of step c).

According to yet a final aspect, the present invention relates to the cosmetic use of an effective amount of complex form(s) in accordance with the invention, as an agent useful for prevent and/or treat the signs of skin ageing.

According to yet another aspect, the present invention relates to the use of an effective amount of complex form(s) in accordance with the invention for preventing and/or treating thinning of an epidermis and/or a loss of firmness, of elasticity, of density, and/or of tonicity of an epidermis and/or the formation of wrinkles and fine lines.

According to yet another aspect, the present invention relates to the use of an effective amount of complex form(s) in accordance with the invention or of at least one agent which modulates the formation of said complex form(s), for preparing and/or improving a pluristratified cell model, in particular a reconstructed skin model.

According to yet another aspect, the present invention relates to a method of preparing an isolated reconstructed skin, comprising at least the step consisting in bringing at least one complex form according to the invention into contact with cells capable of generating an isolated reconstructed skin, and in particular keratinocytes.

Definition of "Complex Forms" of CLSP

As specified above, the complex forms in accordance with the invention derive at least in part from a polypeptide having an amino acid sequence encoded by a nucleic acid sequence represented completely or partly by SEQ ID NO 1, or an analogue thereof or a fragment thereof.

A complex form of CLSP may be in particular a multimer resulting from the association of at least the whole CLSP protein or a fragment thereof with, either itself, or one fragment thereof, or yet with at least one target protein, even with at least one protein structure such as proteolysed cornified envelope in the stratum corneum.

The CLSP fragments according to the invention are fragments having a length and an activity suitable for their implementation as a complex form according to the invention.

More particularly, a complex form of CLSP may be a dimer, and more particularly a whole CLSP homodimer or a fragment thereof.

According to a particular embodiment, a dimer according to the invention may comprise a first monomer represented by the whole CLSP protein or a fragment thereof, and a second monomer represented by a structure distinct from the whole CLSP protein or a fragment thereof.

As examples of monomer represented by a structure distinct from the whole CLSP protein or a fragment thereof suitable for the invention may be mentioned the above-cited proteins and fragments thereof which are able to dimerize with the whole CLSP or a fragment thereof.

According to another particular embodiment, a complex form suitable for the invention may comprise a peptide derived from the CLSP and distinct from the whole CLSP sequence, in particular distinct from the amino acids sequence encoded by a nucleic acid sequence represented by SEQ ID NO 1.

In particular, a peptide derived from the CLSP suitable for the invention may be a fragment of CLSP, and more particularly a fragment of the protein encoded by nucleic acids sequence represented by SEQ ID NO 1, comprising an appropriate length and an activity suitable for its use as a complex form according to the invention.

For the purpose of the present invention, the expression "fragment of a nucleic acid sequence" is intended to denote a nucleic acid sequence partly encoding the complex forms in accordance with the invention, or an analogue thereof, and in particular a nucleic acid sequence represented by SEQ ID NO 1 or an analogue thereof.

The expression "analogue of a nucleic acid sequence" is intended to denote any nucleic acid sequence, optionally resulting from the degeneracy of the nucleic acid code, and encoding at least a part of the complex forms having a sequence identical or analogous to that of the polypeptide encoded by said nucleic acid sequence.

The nucleic acid sequences may be derived from any possible origins, i.e. either animal, in particular mammalian, and even more particularly human or plant, or from microorganisms (viruses, phages, bacteria inter alia) or else from fungi, without prejudging the fact that they may or may not be present naturally in said organism of origin.

According to one variant embodiment, the complex forms according to the invention may be soluble.

For the purpose of the present invention, the term "soluble" is intended to describe the ability of the complexed peptide form under consideration according to the invention to solubilize in water or in an aqueous medium without protein-denaturing substances of the chaotropic agent or ionic detergent type, for example, as opposed to the native CLSP, which can be extracted only in the presence of such agents.

According to another embodiment, the complex forms in accordance with the invention derive at least in part from a polypeptide of which the amino acid sequence is represented completely or partly by SEQ ID NO 2, or an analogue thereof, or a fragment thereof.

For the purpose of the present invention, the term "CLSP" is intended to denote, in general, unless otherwise indicated, the sequence (SEQ ID NO 2) of the protein which may or may not have undergone post-translational modifications of glycosylation type on the asparagine residues in position 25 and/or 43, of phosphorylation type and/or of myristylation type, capable of modifying its apparent molecular weight or its isoelectric point.

It is, moreover, known that the primary sequence of a polypeptide, i.e. the series of its amino acids, determines sites specifically recognized by protease enzymes, such as trypsin which, once the recognition of these sites has become effective, will induce cleavage of the polypeptide by proteolysis. This proteolysis results in the generation of various peptides, or proteolytic fragments, of the complex forms of CLSP.

The inventors have detected the presence of such peptides in the stratum corneum.

Consequently, the invention extends to the complex forms comprising at least a proteolytic fragment of CLSP having the peptide sequence SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24 and SEQ ID NO 25.

Thus, according to one particular embodiment, the complex forms in accordance with the invention derive at least from a polypeptide of which the amino acid sequence is represented completely or partly by an amino acid sequence chosen from SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24 and SEQ ID NO 25, and mixtures thereof.

The term "analogue of a polypeptide" is intended to denote any polypeptide exhibiting a sequence homology, in particular with respect to one of the characteristic sequences of said polypeptide, and also a biological activity of the same nature.

This analogue may be a peptidomimetic agent.

The homology may be at least 85%, for example at least 90%, and for example at least 95%. The homology may be determined by visual comparison or by means of any computer tool generally used in the field, such as the BLAST programs available at www.ncbi.nlm.nih.gov and used with the default parameters.

The sequence homology may result from modifications derived from mutation or variation in the sequences of the peptides according to the invention, originating either from the deletion of one or more amino acids, or from insertion of one or more amino acids, or from the substitution of one or more amino acids in the characteristic sequences of a polypeptide according to the invention.

For the purpose of the invention, the term "fragment" is intended to denote any peptide portion comprising at least 4, at least 6, in particular at least 8, and more particularly at least 12 consecutive amino acids of the CLSP protein, and a substantially similar biological activity.

In general, the polypeptide analogues may comprise conservative substitutions with respect to the natural amino acid sequence.

Several of these modifications may be combined.

By way of example of mutations that may be considered in the present invention, mention may be made, non-exhaustively, of the replacement of one or more amino acid residues with amino acid residues having a similar hydropathic index, without however substantially affecting the biological properties of the complex forms according to the invention.

The hydropathic index is an index assigned to amino acids according to their hydrophobicity and their charge (Kyte et al. (1982), J. Mol. Biol., 157: 105).

The complex forms also covered by the present invention may derive from polypeptides as defined above having undergone one or more post-translational modification(s).

The term "post-translational modification(s)" is intended to encompass all the modifications that a peptide or a protein is capable of undergoing at the end of its synthesis in a cell, such as, for example, one or more phosphorylation(s), one or more thiolation(s), one or more acetylation(s), one or more glycosylation(s), one or more lipidation(s), such as a myristylation, a structural rearrangement such as the formation of disulphide bridges and/or cleavage within the peptide sequence.

The analogue has, moreover, substantially the same biological activity as the natural polypeptide.

According to one embodiment, the complex forms suitable for the implementation of the invention may also derive from natural or synthetic polypeptides, where appropriate capable of being obtained after enzymatic or chemical lysis of the native form of CLSP or by chemical or biological synthesis or by extraction from a biological tissue, for instance the skin, naturally expressing these complex forms, and also the various post-translational forms thereof.

Those skilled in the art can obtain the complex forms in accordance with the invention by means of recombinant DNA based methods, for instance those described in the manual "Molecular Cloning—A Laboratory Manual" (2nd edition), Sambrook et al., 1989, Vol. I-III, Coldspring Harbor Laboratory, Coldspring Harbor Press, NY, (Sambrook).

According to another embodiment, the complex forms suitable for the implementation of the invention may also be fused with another polypeptide distinct from those identified above, a hydrophilic or hydrophobic targeting agent, a bioconversion precursor, or a luminescent, radioactive or colorimetric labelling agent.

In a non-limiting manner, mention may be made, as an example of compounds that can be coupled with the complex forms in accordance with the invention, of fluorescent proteins such as Green Fluorescent Protein, fluorescent chemical compounds such as rhodamine, fluorescein, or Texas Red®, phosphorescent compounds, radioactive elements, such as $^3$H, $^{14}$C, $^{35}$S, $^{121}$I or $^{125}$I, or colorimetric labelling agents such as chromogenic substrates sensitive to the action of galactosidase, of peroxidase, of chloramphenicol acetyltransferase, of luciferase or of alkaline phosphatase.

Depending on the nature of the compounds that can be coupled with the complex forms in accordance with the invention, the coupling may be performed by chemical methods, in particular by means of reactive chemical functions, or by molecular biology methods known to those skilled in the art.

By way of methods for detecting a polypeptide, mention may be made of Western blotting, slot blotting, dot blotting, ELISA (Enzyme Linked Immuno-Sorbent Assay) methods of singleplex or multiplex type, proteomics or glycomics methods, staining of polypeptides in a polyacrylamide gel with a silver-based stain, with Coomassie blue or with SYPRO, immunofluorescence, UV absorption, immunohistochemical methods in conventional, electron or confocal microscopy, FRET (fluorescence resonance energy transfer), TR-FRET (time-resolved FRET) methods, FLIM (fluorescence lifetime imaging microscopy) methods, FSPIM (fluorescence spectral imaging microscopy) methods, FRAP (fluorescence recovery after photobleaching) methods, reporter-gene methods, AFM (atomic force microscopy) methods, surface plasmon resonance methods, microcalorimetry methods, flow cytometry methods, biosensor methods, radioimmunoassay (RIA) methods, isoelectric focusing methods, and enzymatic assays, methods using peptide chips, sugar chips, antibody chips, mass spectrometry methods, and SELDI-TOF spectrometry methods (Ciphergen).

As emerges from what follows, the detection of the complex forms according to the invention is favoured according to an ELISA method.

Use of the Complex Forms According to the Invention, for the Purposes of Diagnosing a State of the Epidermis and/or of Screening for Anti-Ageing Active Agents As specified above, according to another of its aspects, the present invention relates to non-invasive methods for characterizing, in particular in an in vitro or ex vivo manner, the surface state of a nonpathological epidermis or alternatively the effectiveness of a cosmetic or therapeutic treatment, aimed at qualitatively or quantitatively characterizing the expression of the complex forms formed at least in part of CLSP, or from a derivative or fragment thereof.

These methods are particularly advantageous insofar as the implementation thereof does not require obligatory recourse to a surgical technique in order to carry out such a characterization.

The methods according to the invention, described hereinafter, can be carried out on a sample, for example an isolated sample, of epithelium, and in particular of epidermis, taken from an individual.

The methods according to the invention may also be carried out on a sample of epithelium, and in particular of epidermis, taken from an epithelial cell model, and in particular an epidermal cell model, or from a reconstructed isolated skin in order to define the state thereof.

An extract of the epidermis can thus be obtained by simple stripping and directly analysed by the ELISA method as described in Example 1 hereinafter.

The stripping technique consists in applying a sticky surface to the surface of the epidermis, such as Blenderm® from 3M, D'squam (commercial adhesive from CuDERM), or cyanoacrylate glue. By virtue of these strippings, the adherent corneocytes and the content of their intercellular spaces can be sampled and subsequently subjected to an extraction which makes it possible to access the protein content.

The taking of a sample suitable for the method may also be carried out more directly by "washing" the skin surface by means of, for example, accessories of the vane turbine type or of the spiral cell type, as described in patent FR 2 667 778 combined with a fluid circuit, or simply by addition/removal of a drop of buffer at the surface of the skin.

By way of indication of other sampling methods suitable for implementing the invention, mention may be made of methods based on scraping the upper part of the stratum corneum by means of a twin blade system or by shave biopsy. This technique makes it possible to collect squamae which can then be analysed directly by various techniques in order to determine the mineral, amino acid or lipid contents.

At the end of the sampling, the sample is characterized by the ELISA method.

This method is based in particular on the use of antibodies suitable for the detection of complex forms under consideration according to the invention. An antibody capable of being used as a tool for evaluating a state of an epidermis may be obtained by any method known to those skilled in the art, as described in "Antibodies: A Laboratory Manual", Cold Spring Harbor Laboratory Press, Cold Spring Harbor, N.Y. (1990).

As described in Example 1 which follows, the method of detecting the complex forms of CLSP requires in particular the use of two types of monoclonal antibodies, developed by the company covalAb, i.e. a capture antibody (clone DB15C9) and a selection antibody labelled with "sulpho-tag" (CLSP clone DB7g12).

Method for the Diagnosis of a State of the Epidermis

According to one embodiment, a method for characterizing a state of an epithelium, for example an epidermis, comprises at least the steps consisting in:

a) determining, in a surface sample of said epithelium, a content of at least one complex form in accordance with the invention, and b) comparing said content determined in step a) with a reference value.

Advantageously, a method of the invention is noninvasive.

A reference value may, for example, be a content of complex forms, determined on a sample of epidermis taken from an epithelium, and in particular normal skin, i.e. skin which is satisfactory from the physiological point of view, like, for example, young skin.

The measurement of a reference value may be carried out in parallel or sequentially to the determination of said content of said complex forms.

Comparison of a determined content with a reference value may make it possible to evaluate a deviation relative to this value.

The analysis of the size and/or of the nature of this deviation (negative or positive) may be informative with regard to the state of the epidermis.

The characterization of a state of an epidermis may be indicative of a possible skin disorder which may be corrected through the use of compounds capable of modulating the expression of the complex forms under consideration in the invention.

Thus, a decrease in complex form(s) of the invention is indicative of a state of chronological ageing.

According to one embodiment, a method according to the invention may be implemented in a method for the in vivo, in vitro or ex vivo diagnosis of a physiological state of an epithelium, and in particular of the epidermis, with a view in particular to assessing its state of chronobiological ageing and, for example, its associated deficiencies and/or alterations in an individual.

Screening for Biological or Chemical Compounds

The present invention relates to the use of the complex forms in accordance with the invention, as a tool for screening for biological or chemical compounds capable of modulating an increase in and/or the stability and/or the biological activity of these complex forms.

The present invention also relates to a method of screening for biological or chemical compounds, or even anti-ageing active agents, or physicochemical factors, capable of modulating the amount of the complex forms in accordance with the invention, comprising at least the steps consisting in:

a) bringing at least one cell type containing at least one complex form in accordance with the invention into contact with at least one test chemical or biological compound, under conditions suitable for the release of said complex form, b) determining a content of said complex form, and c) comparing said content determined in step b) with a content of said complex form determined in the absence of test chemical or biological compound.

The comparison carried out in step c) may make it possible to deduce information regarding the property of said tested compound of modulating the expression of the complex forms in accordance with the invention.

As specified above, this method may also comprise a step aimed at retaining the active agents for which an increase in the content of complex form(s) is observed.

More particularly, the method that is of use for characterizing the effectiveness of a treatment capable of preventing and/or treating the signs of skin ageing in an individual, may comprise at least the steps consisting in:

i. providing at least a first skin surface sample representative of said individual, ii. quantifying, in said sample, especially via the ELISA assay technique disclosed in Example 1, at least one complex form under consideration in the present invention, iii. repeating steps i. and ii. on a second skin surface sample representative of said individual, and iv. comparing the results obtained at the end of steps ii. and iii., in particular in order to deduce therefrom information relating to at least one effect of the treatment, said first and second skin surface samples corresponding to different treatment stages.

In the event that a reference value measurement is carried out prior to the use of the test biological or chemical compound or of the test physicochemical factor, the method according to the invention may also make it possible, where appropriate, to assess the potential effectiveness of said compound.

This amount may not be affected by the presence of said compound or on the other hand, may be inhibited or stimulated.

In the event that an increase is observed, the compound tested is capable of being used, for example, as an anti-ageing active agent.

According to one variant embodiment, the methods as defined above may also comprise at least one step consisting of administering to an individual, a cosmetic care composition established or selected with regard to the information obtained at the end of step iv.

The determination of a content of the complex forms in accordance with the invention is carried out by means of an ELISA method, in particular that specifically described in Example 1 hereinafter.

According to another of the aspects of the present invention, the complex forms of CLSP as described above may be used in a cosmetic or therapeutic composition.

It is understood that all the cosmetic or therapeutic compositions under consideration according to the invention use a physiologically acceptable medium.

For the purpose of the present invention, the term "physiologically acceptable medium" is intended to denote a medium that is suitable for application of a composition to an epithelium or a keratin material, such as the skin, the scalp, the lips, the mucous membranes and keratin fibres such as the hair, the nails and body hair or, where appropriate, orally or parenterally.

For the purpose of the invention, the term "cosmetic" is intended to denote a use intended, principally, to provide an aesthetic and/or comfort effect.

For the purpose of the present invention, the term "therapeutic" is intended to denote a composition that can be used in the context of a prophylactic and/or curative treatment, or of a method for evaluating a state of an epithelium, and in particular of the epidermis.

For the purpose of the invention, the term "prophylactic" or "preventive" is intended to mean the decreased risk of occurrence of a phenomenon, for example a pathological condition.

According to another embodiment, a cosmetic or therapeutic composition in accordance with the invention may also comprise at least one cosmetic and/or therapeutic active agent.

As examples of active agents that can be used in the context of the present invention, mention may be made of cosmetic oils, such as silicone oils, plant oils of triglyceride type, hydrocarbon-based oils such as parleam oil and esters of fatty acids and of fatty alcohols.

Other active agents which make it possible to improve the state of the skin may also be used, such as moisturizing active agents, or active agents which make it possible to improve the natural lipid barrier, such as ceramides, cholesterol sulphates and/or fatty acids and mixtures thereof.

It may also be possible to use enzymes which have an activity on the skin, such as proteases, lipases, glucosidases, amidases, cerebrosidases and/or melanases, and mixtures thereof.

In general, any composition of the invention may be applied to the skin (on any cutaneous region of the body) or to the mucous membranes (buccal, jugal, gingival, genital, conjunctival, etc.).

In a known manner, a cosmetic composition may also contain adjuvants which are customary in the cosmetics field, such as hydrophilic or lipophilic gelling agents, hydrophilic or lipophilic additives, preservatives, antioxidants, solvents, fragrances, fillers, screening agents, odour absorbers and dyestuffs.

The amounts of the various constituents of the compositions according to the invention are those conventionally used in the fields under consideration.

The amount of complex form(s) in accordance with the invention, contained in a composition according to the invention, also referred to as "effective amount" of course depends on the nature of the compound and on the desired effect, and may therefore vary to a large extent.

To give an order of magnitude, a composition may contain a complex form according to the invention in an amount representing from 0.00001% to 50% of the total weight of the composition, in particular in an amount representing from 0.001% to 10% of the total weight of the composition, and more particularly in an amount representing from 0.1% to 1% of the total weight of the composition.

A composition according to the invention may be more particularly intended for reducing and/or treating conditions that may cause deterioration of the state of an epithelium, and in particular of an epidermis.

Such a state may be of chronological origin (i.e. linked to the time that has passed, such as skin ageing) and/or indicative of a skin disorder, linked for example to photoageing.

Thus, a composition in accordance with the invention, especially a cosmetic composition, may in particular be for use in preventing and/or treating thinning of an epidermis and/or a loss of firmness, of elasticity, of density and/or of tonicity of an epidermis and/or the formation of wrinkles and fine lines.

According to another embodiment, a composition in accordance with the invention, in particular a cosmetic composition, may, especially, be for use in preventing and/or treating cutaneous sign of dryness, in particular in preventing and/or treating dehydration of an epidermis.

According to another embodiment, a composition in accordance with the invention, especially a cosmetic composition, may be for use in preventing and/or treating signs of epidermal ageing.

According to another aspect, the present invention relates to a method for the cosmetic treatment of the signs of skin ageing, comprising at least one step consisting in applying at least one cosmetic composition in accordance with the invention to at least a part of the skin, the mucous membranes and/or the keratin fibres.

According to yet another aspect, the invention also relates to the use, in particular cosmetic and/or therapeutic use, of complex forms of the CLSP protein, of peptide fragments of this protein or of analogues thereof, or of an agent which modulates the activity, the expression and/or the stability of such a polypeptide, in particular for preventing the signs of skin ageing, in particular for preventing and/or treating aged skin.

The present invention also relates to the use of an effective amount of complex forms in accordance with the invention for preparing and/or improving a pluristratified cell model, especially of epidermal or mucosal type, and in particular a reconstructed skin model.

For the purpose of the invention, the term "reconstructed skin model" is intended to denote a model in which various cell types, such as in particular the natural constituents of the skin, like, for example, keratinocytes, fibroblasts, Langerhan cells and melanocytes, are combined.

The fibroblast cells may or may not be irradiated.

Such models and the preparation thereof are known to those skilled in the art.

Thus, the present invention is also directed towards a method of preparing an isolated reconstructed skin, comprising at least the step consisting in bringing at least one complex form according to the invention into contact with cells capable of generating an isolated reconstructed skin, and in particular keratinocytes.

The examples and figures which follow are presented by way of nonlimiting illustration of the invention.

Example 1

Development of a High-Sensitivity ELISA Assay for Assaying Complex Forms of CLSP in Accordance with the Invention:

CLSP plates developed, custom-made, with the MesoScale Discovery (MSD) technology were used in this assay. The monoclonal antibodies directed against a recombinant "full-length" CLSP protein fused with GST were developed by the company CovalAb (Lyon, France) (Méhul et al., 2006). The capture antibody (Clone DB15C9) was deposited at a concentration of 200 µg/ml on a standard 96-well plate of "small spot" type (MesoScale).

A reference curve (5 to 0.078 µg/ml) was established using the recombinant CLSP protein.

Each plate was blocked with a blocking buffer (MesoScale) for 1 hour at ambient temperature. 25 µl of each sample and of standards were deposited in triplicate and incubated with stirring for 1 hour at ambient temperature. The plate was then washed 4 times with Tris buffer (MesoScale). The plates were then incubated with stirring for 1 hour at ambient temperature with 25 µl of detection antibody (Mesoscale) labelled with "sulpho-tag" (CLSP clone DB7g12) at a concentration of 1 µg/ml. The plates were washed 4 times with a Tris buffer (MesoScale) before the addition of 150 μl of 1× read buffer T (MesoScale). The plates were read on the "Sector Imager 6000" instrument. The data was standardized in terms of ng CLSP per μg of total protein.

Example 2

Characterization of the Content of CLSP Complex Forms in Various Samples Taken by Stripping This characterization is carried out by means of the ELISA assay described in Example 1.

Two clinical studies were carried out: a knowledge study (2 groups of 20 female individuals, with Caucasian skin: 30-35 years old and 60-65 years old) with samples taken from the forearm and the face, and a product study over 56 days, i.e. 2 months (1 group of 24 female individuals, with Caucasian skin, aged 40-45) with samples taken only from the forearm.

The product is a serum composed of 10% of bifidiobiotic (CLR complex) and 0.002% of phytosphingosine-SLC (treatment "G").

The CLR complex relates to a lysate registered under the INCI name: Bifidat ferment Lysate, under the EINECS name: Bifidobacterium longum, under the EINECS No.: 306-168-4 and under CAS No.: 96507-89-0.

Such a lysate is in particular sold under the name Repair Complex CLR® by the company K. Richter GmbH.

The name Phytosphingosine-SLC corresponds to a phytosphingosine-salicylate derivative sold by the company Evonik Goldschmidt.

For both studies, D-squame samples were taken from the face (cheek) and from the forearm (posterior face). The D-squame corneodiscs sampled from the forearms were used to evaluate the product effects.

a) Extraction of the Proteins from the D-Squame Corneodiscs:

The corneodisc is placed in a 2 ml Eppendorf tube, sticky surface facing inwards, to which 550 μl of "Native+" extraction buffer (TBS, 1% TRITON™ X-100, 1M NaCl) and one stainless steel bread per tube are added. The tube is then placed in the racks of the MM400 vibration mill (Retsch). The extraction is carried out by vibration milling for one cycle of 2 min at 30 Hz. The medium is then recovered and filtered through a 0.45 μm Millipore Ultrafree column, followed by centrifugation for 5 min at 5000 g at 4° C. The supernatant is stored at −20° C. while waiting to be analysed.

b) Statistical Analysis

The analysis of the biomarkers for the age (young vs. aged) and region (arm vs. face) effects is carried out by means of a mixed model of analysis of variance with the age, region and age*region interaction factors as fixed effects, and the subject factor as random effect. The region effect for an age category and the age effect for a region were realized by means of contrasts.

The analysis of the biomarkers, for the treatment effect, is carried out by means of a mixed model of analysis of variance on the paired active agent-placebo differences with the time factor as fixed effect and the subject factor as random effect.

The treatment effect at D0 and D56 is tested by means of contrasts.

The variables were, when necessary, log-transformed beforehand in order to make their distribution more Gaussian.

The SPSS software, version 14 is used for the descriptive analyses (graphs of the means and box plots), and the SAS Enterprise Guide software, version 3 is used for the interference part.

The first-species alpha-risk was fixed at 5% in a two-sided approach.

Figure 2:
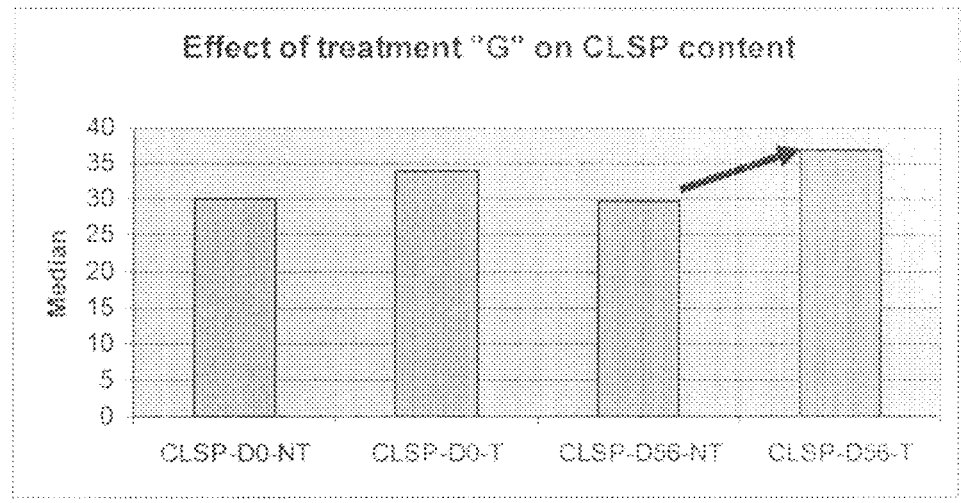
FIG. 2: it illustrates the effects linked to the application of a cosmetic composition, composed of 10% of bifidiobiotic (CLR complex) and 0.002% of phytosphingosine-SLC (treatment "G"), on the amount of complex forms according to the invention, in the skin of the forearm and of the face.

The results of these two studies are given in FIGS. 1 and 2.

The data reveal a decrease in the complex forms of CLSP with age, as represented in FIG. 1.

The high-sensitivity ELISA kit that was developed indeed makes it possible to verify that the expression of the complex forms of CLSP decreases with age.

FIG. 2, for its part, represents the effect of the tested product on the amount of complex forms. A significant increase in the amount of complex forms is clearly observed, thereby demonstrating the activating effect of this product. The latter therefore provides a real anti-ageing effect.

The invention claimed is:

1. A method of screening for anti-ageing active agents, comprising:
   a) bringing at least one cell type containing at least one complex form of calmodulin-like skin protein, or CLSP, which is a polypeptide comprising an amino acid sequence as set forth in SEQ ID NO:2 or an analogue thereof, or a fragment thereof, into contact with at least one test anti-ageing active agent, under conditions suitable for the expression of said complex form,
   said analogue having a sequence homology with SEQ ID NO: 2 of at least 90%;
   said fragment thereof being selected from the group of sequences consisting of the peptide sequences SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24 and SEQ ID NO 25;
   wherein the complex form is a conjugate of the CLSP protein with another protein distinct from CLSP or with a CLSP protein or a fragment thereof,
   b) determining a content of said complex form, and
   c) comparing said content determined in step b) with a content of said complex form determined in the absence of test chemical or biological compound,
   wherein an increase in complex form(s) of calmodulin-like skin protein is indicative of an active agent with anti-ageing properties.

2. A method for screening for biological or chemical compound capable of modulating the increase in and/or the stability and/or the biological activity of at least one complex form of calmodulin-like skin protein, or CLSP, which is a polypeptide comprising an amino acid sequence as set forth in SEQ ID NO2 or an analogue thereof, or a fragment thereof,
   said analogue having a sequence homology with SEQ ID NO: 2 of at least 90%;
   said fragment thereof being selected from the group of sequences consisting of the peptide sequences SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24 and SEQ ID NO 25;
   wherein said complex form is any conjugate of the CLSP protein with either another protein distinct from CLSP or with another CLSP protein or a fragment thereof,
   comprising contacting at least said complex form with at least one biological or chemical compound to be screened, wherein an increase in complex form(s) of CLSP is indicative of an active agent with anti-ageing properties.

* * * * *

SEQUENCE LISTING

```
<160> NUMBER OF SEQ ID NOS: 25

<210> SEQ ID NO 1
<211> LENGTH: 858
<212> TYPE: DNA
<213> ORGANISM: Homo Sapiens

<400> SEQUENCE: 1
aattcccgga tccctgcggc tgcctgcact ctggaccacg agctctgaga gcagcaggtt      60
gagggccggt gggcagcagc tcggaggctc cgcgaggtgc aggagacgca ggcatggccg     120
gtgagctgac tcctgaggag gaggcccagt acaaaaaggc tttctccgcg gttgacacgg     180
atggaaacgg caccatcaat gcccaggagc tgggcgcggc gctgaaggcc acgggcaaga     240
acctctcgga ggcccagcta aggaaactca tctccgaggt tgacagcgac ggcgacggcg     300
aaatcagctt ccaggagttc ctgacggcgg caaggaaggc cagggccggc ctggaggacc     360
tgcaggtcgc cttccgcgcc ttcgaccagg atggcgacgg ccacatcacc gtggacgagc     420
tcaggcgggc catggcgggg ctggggcagc cgctgccgca ggaggagctg gacgccatga     480
```

```
tccgcgaggc cgacgtggac caggacgggc gggtgaacta cgaggagttc gcgaggatgc      540
tcgcccagga gtgaggctcc ccgcctgtgt ccccctggct gcgctctgag ccttcagggc      600
caccgcccgc tgctgctttt gtgctgggac tctccgggga aacctggtcg gtggatggga      660
aactgcctcc ccctgggagg aaggctttgc gctccggggc ctggatgcgg cgccctcggg      720
ccgcctgcga gcccctctct gccttcagac cttgggcaga aggaggcctc cttgggcctg      780 gtccccmcttt gccctgcagt ggaatgaggg ccccttaacc ccgcattgat ctaaataaag      840
gactgccgag ttccaaaa                                                    858
```

```
<210> SEQ ID NO 2
<211> LENGTH: 146
<212> TYPE: PRT
<213> ORGANISM: Homo Sapiens

<400> SEQUENCE: 2

Met Ala Gly Glu Leu Thr Pro Glu Glu Ala Gln Tyr Lys Lys Ala
1               5                   10                  15

Phe Ser Ala Val Asp Thr Asp Gly Asn Gly Thr Ile Asn Ala Gln Glu
                20                  25                  30

Leu Gly Ala Ala Leu Lys Ala Thr Gly Lys Asn Leu Ser Glu Ala Gln
                35                  40                  45

Leu Arg Lys Leu Ile Ser Glu Val Asp Ser Asp Gly Asp Gly Glu Ile
            50                  55                  60

Ser Phe Gln Glu Phe Leu Thr Ala Ala Arg Lys Ala Arg Ala Gly Leu
65                  70                  75                  80

Glu Asp Leu Gln Val Ala Phe Arg Ala Phe Asp Gln Asp Gly Asp Gly
                85                  90                  95

His Ile Thr Val Asp Glu Leu Arg Arg Ala Met Ala Gly Leu Gly Gln
                100                 105                 110

Pro Leu Pro Gln Glu Glu Leu Asp Ala Met Ile Arg Glu Ala Asp Val
            115                 120                 125

Asp Gln Asp Gly Arg Val Asn Tyr Glu Glu Phe Ala Arg Met Leu Ala
        130                 135                 140

Gln Glu
145
```

```
<210> SEQ ID NO 3
<211> LENGTH: 16
<212> TYPE: PRT
<213> ORGANISM: Homo Sapiens

<400> SEQUENCE: 3

Ala Phe Asp Gln Asp Gly Asp Gly His Ile Thr Val Asp Glu Leu Arg
1               5                   10                  15
```

```
<210> SEQ ID NO 4
<211> LENGTH: 17
<212> TYPE: PRT
<213> ORGANISM: Homo Sapiens

<400> SEQUENCE: 4

Ala Phe Asp Gln Asp Gly Asp Gly His Ile Thr Val Asp Glu Leu Arg
1               5                   10                  15

Arg
```

```
<210> SEQ ID NO 5
<211> LENGTH: 16
```

-continued

```
<212> TYPE: PRT
<213> ORGANISM: Homo Sapiens

<400> SEQUENCE: 5

Ala Phe Ser Ala Val Asp Thr Asp Gly Asn Gly Thr Ile Asn Ala Gln
1               5                   10                  15

<210> SEQ ID NO 6
<211> LENGTH: 23
<212> TYPE: PRT
<213> ORGANISM: Homo Sapiens

<400> SEQUENCE: 6

Ala Phe Ser Ala Val Asp Thr Asp Gly Asn Gly Thr Ile Asn Ala Gln
1               5                   10                  15

Glu Leu Gly Ala Ala Leu Lys
            20

<210> SEQ ID NO 7
<211> LENGTH: 13
<212> TYPE: PRT
<213> ORGANISM: Homo Sapiens

<400> SEQUENCE: 7

Ala Gly Glu Leu Thr Pro Glu Glu Glu Ala Gln Tyr Lys
1               5                   10

<210> SEQ ID NO 8
<211> LENGTH: 14
<212> TYPE: PRT
<213> ORGANISM: Homo Sapiens

<400> SEQUENCE: 8

Ala Gly Glu Leu Thr Pro Glu Glu Glu Ala Gln Tyr Lys Lys
1               5                   10

<210> SEQ ID NO 9
<211> LENGTH: 11
<212> TYPE: PRT
<213> ORGANISM: Homo Sapiens

<400> SEQUENCE: 9

Ala Gly Leu Glu Asp Leu Gln Val Ala Phe Arg
1               5                   10

<210> SEQ ID NO 10
<211> LENGTH: 19
<212> TYPE: PRT
<213> ORGANISM: Homo Sapiens

<400> SEQUENCE: 10

Ala Met Ala Gly Leu Gly Gln Pro Leu Pro Gln Glu Glu Leu Asp Ala
1               5                   10                  15

Met Ile Arg

<210> SEQ ID NO 11
<211> LENGTH: 9
<212> TYPE: PRT
<213> ORGANISM: Homo Sapiens

<400> SEQUENCE: 11

Glu Ala Asp Val Asp Gln Asp Gly Arg
1               5
```

```
<210> SEQ ID NO 12
<211> LENGTH: 24
<212> TYPE: PRT
<213> ORGANISM: Homo Sapiens

<400> SEQUENCE: 12

Lys Ala Phe Ser Ala Val Asp Thr Asp Gly Asn Gly Thr Ile Asn Ala
1               5                   10                  15

Gln Glu Leu Gly Ala Ala Leu Lys
            20

<210> SEQ ID NO 13
<211> LENGTH: 24
<212> TYPE: PRT
<213> ORGANISM: Homo Sapiens

<400> SEQUENCE: 13

Lys Leu Ile Ser Glu Val Asp Gly Asp Gly Asp Gly Glu Ile Ser Phe
1               5                   10                  15

Gln Glu Phe Leu Thr Ala Ala Arg
            20

<210> SEQ ID NO 14
<211> LENGTH: 15
<212> TYPE: PRT
<213> ORGANISM: Homo Sapiens

<400> SEQUENCE: 14

Lys Leu Ile Ser Glu Val Asp Ser Asp Gly Asp Gly Glu Ile Ser
1               5                   10                  15

<210> SEQ ID NO 15
<211> LENGTH: 24
<212> TYPE: PRT
<213> ORGANISM: Homo Sapiens

<400> SEQUENCE: 15

Lys Leu Ile Ser Glu Val Asp Ser Asp Gly Asp Gly Glu Ile Ser Phe
1               5                   10                  15

Gln Glu Phe Leu Thr Ala Ala Lys
            20

<210> SEQ ID NO 16
<211> LENGTH: 24
<212> TYPE: PRT
<213> ORGANISM: Homo Sapiens

<400> SEQUENCE: 16

Lys Leu Ile Ser Glu Val Asp Ser Asp Gly Asp Gly Glu Ile Ser Phe
1               5                   10                  15

Gln Glu Phe Leu Thr Ala Ala Arg
            20

<210> SEQ ID NO 17
<211> LENGTH: 23
<212> TYPE: PRT
<213> ORGANISM: Homo Sapiens

<400> SEQUENCE: 17

Leu Ile Ser Glu Val Asp Gly Asp Gly Asp Gly Glu Ile Ser Phe Gln
1               5                   10                  15

Glu Phe Leu Thr Ala Ala Arg
```

20

<210> SEQ ID NO 18
<211> LENGTH: 12
<212> TYPE: PRT
<213> ORGANISM: Homo Sapiens

<400> SEQUENCE: 18

Leu Ile Ser Glu Val Asp Ser Asp Gly Asp Gly Glu
1               5                   10

<210> SEQ ID NO 19
<211> LENGTH: 23
<212> TYPE: PRT
<213> ORGANISM: Homo Sapiens

<400> SEQUENCE: 19

Leu Ile Ser Glu Val Asp Ser Asp Gly Asp Gly Glu Ile Ser Phe Gln
1               5                   10                  15

Glu Phe Leu Thr Ala Ala Lys
            20

<210> SEQ ID NO 20
<211> LENGTH: 23
<212> TYPE: PRT
<213> ORGANISM: Homo Sapiens

<400> SEQUENCE: 20

Leu Ile Ser Glu Val Asp Ser Asp Gly Asp Gly Glu Ile Ser Phe Gln
1               5                   10                  15

Glu Phe Leu Thr Ala Ala Arg
            20

<210> SEQ ID NO 21
<211> LENGTH: 8
<212> TYPE: PRT
<213> ORGANISM: Homo Sapiens

<400> SEQUENCE: 21

Asn Leu Ser Glu Ala Gln Leu Arg
1               5

<210> SEQ ID NO 22
<211> LENGTH: 8
<212> TYPE: PRT
<213> ORGANISM: Homo Sapiens

<400> SEQUENCE: 22

Asn Leu Ser Glu Ala Gln Leu Arg
1               5

<210> SEQ ID NO 23
<211> LENGTH: 12
<212> TYPE: PRT
<213> ORGANISM: Homo Sapiens

<400> SEQUENCE: 23

Ser Ala Val Asp Thr Asp Gly Asn Gly Thr Ile Asn
1               5                   10

<210> SEQ ID NO 24
<211> LENGTH: 21
<212> TYPE: PRT
<213> ORGANISM: Homo Sapiens

```
<400> SEQUENCE: 24

Ser Ala Val Asp Thr Asp Gly Asn Gly Thr Ile Asn Ala Gln Glu Leu
1               5                   10                  15

Gly Ala Ala Leu Lys
            20

<210> SEQ ID NO 25
<211> LENGTH: 8
<212> TYPE: PRT
<213> ORGANISM: Homo Sapiens

<400> SEQUENCE: 25

Val Asn Tyr Glu Glu Phe Ala Arg
1               5
```